United States Patent [19]

Csatar et al.

[11] 3,966,641

[45] June 29, 1976

[54] SORPITIONAL CARRIER MATERIALS AND A PROCESS FOR THE PREPARATION THEREOF

[75] Inventors: Kálmán Csatar; István Soha, both of Budapest, Hungary

[73] Assignee: Országos Érc- és Ásványbányák, Budapest, Hungary

[22] Filed: Feb. 27, 1975

[21] Appl. No.: 553,552

[30] Foreign Application Priority Data

Mar. 6, 1974 Hungary.............................. CA 363

[52] U.S. Cl................................. 252/449; 252/448; 252/455 R; 71/62
[51] Int. Cl.² ................... B01J 21/08; B01J 29/00; B01J 29/06
[58] Field of Search............... 252/448, 449, 455 R; 71/64 SC, 62

[56] References Cited
UNITED STATES PATENTS

| | | | |
|---|---|---|---|
| 1,985,526 | 12/1934 | Stockton............................ | 252/449 |
| 2,691,598 | 10/1954 | Meurice et al...................... | 252/449 |
| 2,698,815 | 1/1955 | Bishop............................... | 252/448 |
| 2,967,154 | 1/1961 | Beerman............................ | 252/449 X |

*Primary Examiner*—Carl F. Dees
*Attorney, Agent, or Firm*—Karl F. Ross; Herbert Dubno

[57] ABSTRACT

The invention relates to a porous carrier rock-based sorptional carrier containing at least one porous carrier rock in an amount not exceeding 95 % by weight, and 5 to 30 % by weight of montmorillonite and optionally illite and/or kaolinite and/or a co-mineral of the latter, with the proviso that a montmorillonite content of at least 5 % by weight is provided for. These carriers have a multiple sorptional pore space, possess a sorption capacity of at least 50 %, and are quasi-spherical in shape.

The above carriers can be prepared, in accordance with the invention, as follows: at least one porous carrier rock is suspended in water either directly or after pre-crushing, then, if not contained originally in the carrier rock in the appropriate amount and ratio, 5 to 30 % by weight, calculated for the amount of the carrier rock, of montmorillonite and optionally illite and/or kaolinite and/or a co-mineral of the latter is added to the suspension as plastic clay mineral also capable of binding in wet state, with the proviso that a montmorillonite content of at least 5 % by weight is provided for the carrier rock, thereafter the total dry material content of the suspension is adjusted to at least 30 % by weight, the suspension is homogenized, is subjected to spray-drying, and, if desired, the obtained particles are fired at 900° to 1300°C.

The carriers according to the invention can be used to great advantages in combination with biologically active substances, such as herbicidal, pesticidal, etc. agents.

6 Claims, No Drawings

SORPTIONAL CARRIER MATERIALS AND A PROCESS FOR THE PREPARATION THEREOF

This invention relates to sorptional carrier materials for use in combination with biologically active substances. The invention relates further to a process for the preparation of such sorptional carrier materials.

As is known, biologically active substances are generally formulated, prior to their utilization, with a suitable chemically inert carrier. As a result of this formulation the biologically active substances (termed in the following as active agents), which are often highly toxic, inflammable and/or liable to decomposition, become safe to handle and store, and can be utilized in any method of treatment, such as in machine spraying or admixing with the soil. The active agent is liberated from the carrier substance in the soil or in the biological environment of the plants, and exerts its effects in accordance with its specific chemical properties.

It is also known that solid or liquid, natural or synthetic, organic or inorganic substances can equally be utilized to formulate the active agents. Of the solid inorganic substances of natural occurrence substances of mineral origin, such as bentonite, fuller's earth, sepiolite, attapulgite, kaolin, illite, halloysite, clay minerals, chalk and other biogeneous limes, pumices, expanded perlite and vermiculite, and, most preferably, silicic earths are the most widespread carriers.

Carrier substances possessing appropriate porosity to bind the active agent are termed as "sorptional carriers". The majority of mineral carriers belong to this class, of which the silicic earths with the highest porosity and sorption capacity, i.e. diatomaceous earths, are the most suitable ones. According to the recent teaching e.g. blister basalt and other porous-bubble volcanic rocks, volcanic tuffs and several sand rock types can also be regarded as porous minerals.

Several methods are known for the preparation of sorptional carriers. The most simple of these techniques consists in pre-crushing the mined rock, optionally drying it, granulating the rock by grinding, and grading the ground substance. This technique is used for the processing of the "standing ground" (grindable and granulable rocks), such as pumice stone, chalk and other limestone types, tuffs, lava rocks, perlite and vermiculite. This method for the preparation of carriers is, however, very energy-consuming, hazardous to the environment and to the workers because of powder formation, and operates with considerable losses (about 15 to 35 %). A further disadvantage of this method is that, owing to the morphological properties of the obtained carrier particles, i.e. their angled or splintery shape and rough surfaces, the free-flowing characteristics of the carrier are poor, and its abrasion effect is strong, which has an adverse effect on both the homogeneous sorption of the active agent and the machine application technology. These morphological properties can be improved for instance by secondary abrasion, but these processes are expensive, hazardous, and time-consuming operations.

A second known method for the production of sorptional carriers, the "build-up" granulation technology, is even more expensive and more hazardous to the environment than the above technique. According to this latter method the pre-crushed and dried rock is finely ground to obtain a gound material with a particle size of maximum $100/\mu$. There after the active agent and a binding agent, as well as optionally a surface-active agent and/or one or more other modifying agent(s) are admixed either simultaneously or in consecutive steps with the finely ground rock, and finally the obtained mixture is granulated either by conventional techniques or by fluidization. It is a further disadvantage of this method, that the pore space distribution of the carrier particles is relatively uniform in the entire granulated mass as a result of agglomeration due to the fine grinding and to the mechanical motion and the collision and friction of the particles against one and against the walls of the apparatus. Furthermore, due to the agglomeration of particles the complete penetration, thus the complete utilization of the spaces by the active agent, cannot be ensured.

A further known method is the thermal agglomeration of minerals. In this method the minerals are heated to the temperature of surface softening, and thus certain "ceramic bonds" are formed between the adjacent mineral particles. This method is applied to the processing of rocks which consist originally of fine particles unsuitable for the production of carriers. Such minerals are certain types of silicic earth, fine pumice sand, and certain rock flours. Thermal agglomeration is performed generally by pre-crushing the crude rock to a maximum particle size of 20 to 30 mm., and firing the crushed particles in a tumbling furnace at an appropriate temperature to form the ceramic bonds. In this operation it must be ensured that all particles reach uniformly the same temperature. The resulting clumpy agglomerate is ground subsequently to the desired particle size, and the ground material is graded. The major disadvantages of this method are the high cost, the high energy requirement, the serious environmental pollution caused, and when silicic earth is used as the starting substance — the high risk of silicosis. The grinding and grading operations involve considerable (at least 20 to 35 %) loss. The obtained carrier particles are particularly angular in shape, their surfaces are rough, and thus their free-flowing characteristics are completely insufficient. Although the thus-obtained particles relatively well retain the original sedimentation-genetic structure of the starting rocks, their pore spaces are, like those of the carriers obtained by build-up granulation, only partially available for the penetration of active agent.

It is also known that formulations ready for use, i.e. compositions already containing the active agent, can be prepared by admixing the ingredients with each other in the form of a suspension, and forming granulates from the suspension by spray-drying. In this method the rock carrier is subjected to a prior fine grinding, is suspended in an appropriate medium, the active agent and the other additives are mixed into the suspension, and finally the suspension is spray-dried. According to another embodiment of this method a pre-crushed carrier material is admixed with the active agent and the additives, the mixture is subjected to wet grinding, and finally the resulting suspension is spray-dried. Such spray-drying techniques are described in the Hungarian patent specification No. 159,751, German patent specifications Nos. 1,905,524 and 1,812,574, Swiss patent specifications Nos. 225,618, 502,765 and 531,701, and in British patent specifications Nos. 1,281,653 and 1,288,094. The spraying techniques in which a suspension also containing the active agent is used have as their main disadvantage that the choice of active agents is limited because in these processes only solid active agents melting above 200°C and not liable to thermal decomposition can be formulated. A further disadvantage of the spray-drying technique is that it generally provides small particles, of a maximum of 0.4 mm. in diameter, which have too low weight and thus cannot be used in the most up-to-date application methods, e.g. in aircraft spraying.

A further known method of preparing supported active agents consists in spraying a solution of the active agent onto kaolin, evaporating the solvent, and granulating the obtained substance (Hungarian patent specification No. 161,561).

Now it has been found, unexpectedly, that sorptional carriers free of the disadvantages of the known carriers, with a sorption capacity of at least 50 %, with a multiple sorptional pore space, and with quasi-spherical shape can be prepared by suspending in water, preferably by wet grinding, at least one carrier mineral of porous structure hereafter described as "carrier rock" either directly or after pre-crushing. Then, if not contained originally in the carrier rock in the appropriate amount and ratio, adding to the suspension as plastic clay mineral also capable of binding in wet state 5 to 30 %, preferably 8 to 20 %, calculated for the amount of the carrier rock, of montmorillonite and/or illite and/or kaolinite and/or a co-mineral of the latter, such as dickite, nackrite or, fireclay provided that a montmorillonite content of at least 5 % is provided for the carrier rock. Thereafter the total dry substance content of the suspension is adjusted to at least 30 %, the suspension being homogenized by intense stirring, subjected to spray-drying to obtain particles of 0.1 to 1.5 mm. in diameter. If desired the particles are subjected, preferably in a continuous way, to firing at a temperature corresponding to the surface softening of the mineral particles of the grain, whereby they become durably strengthened.

Thus, on one hand, the invention relates to a porous rock-based sorptional carrier. The sorptional carrier according to the invention contains at least one porous carrier rock in an amount not exceeding 95 % by weight and 5 to 30 % by weight of montmorillonite and optionally illite and/or kaolinite and/or a co-mineral of the latter, with the proviso that the montmorillonite content is at least 5 % by weight, and that said sorptional carrier has a sorption capacity of at least 50 %, has a multiple sorptional pore space and is quasi-spherical in shape.

The carrier substance according to the invention may contain, as carrier rock, e.g. silicic earth (diatomaceous earth), pumices, tuffs, bubble-porous lava rocks, expanded perlite or vermiculite, chalks or other porous biogeneous lime, porous sand rock and other similar cementation granular rocks. Of these carrier rocks silicic earth has proved to be very advantageous.

Owing to their quasi-spherical shape, the particles of the carriers according to the invention possess good free-flowing characteristics. These carrier substances are chemically completely inert, have a sorption capacity of at least 50 %, and possess a completely permeable pore space directly contacting with the environment over the entire volume, thus ensuring easy desorption and an appropriate desorption rate for the active agent. This latter characterisitc is presumably due to the fact that the colloidal solution of the plastic clay minerals, also capable of binding in wet state and having a high degree of dispersity in water (containing mostly particles of 0.1 to 1 $\mu$ in diameter), sets the surface tension of water and the viscosity of the suspension to an optimum value, and thus ensures a movement of the porous rock particles during the drop formation upon spraying and during the grain formation upon drying the droplets so that the structure of the obtained grain is denser at the surface and becomes gradually less dense towards the center. Thus this internal structure contains an almost homodispersion primary pore space contributed by the own porosities of the carrier rock particles, which is in direct contact with the secondary pore space between the particles connected to each other in a lattice. This complex pore space is completely permeable in every direction. This pore structure is completely reproducible in every grain and in every batch, and it ensures the full availability of the grains for binding the active agent. Furthermore, this pore structure also enables to application of two different active agents to the carrier grain by utilizing the primary and secondary pore spaces, i.e. to obtain a formulation of dual action; it also makes it possible to adsorb even a third active agent onto the surface owing to the high adsorption capacity of the surface of the grain.

As mentioned above, the invention also relates to the preparation of a sorptional carrier having the above characteristics. These carrier substances are prepared, in accordance with the invention, as follows: at least one porous carrier rock (as described) is suspended in water preferably by wet grinding either directly or after pre-crushing; then, if not contained originally in the carrier rock in the appropriate amount and ratio, 5 to 30 %, preferably 8 to 20 % by weight, calculated for the amount of the carrier rock, of montmorillonite and optionally illite and/or kaolinite and/or a co-mineral of the latter is added to the suspension as as plastic clay mineral also capable of binding in wet state provided that a montmorillonite content of at least 5 % by weight is provided for the carrier rock. Thereafter the total dry substance content of the suspension is adjusted to at least 30 % by weight, the suspension is homogenized preferably by intense stirring, is subjected subsequently to spray-drying to obtain particles of 0.1 to 1.5 mm. in diameter, and, if desired, the obtained particles are fired at 900° to 1300°C, preferably in a continuous operation.

Spray-drying is carried out in accordance with the invention by known spraying equipment or spraying towers. In order to ensure the formation of grains of the desired dimensions preferably nozzle spraying is used, and the diameter of the nozzle is adjusted preferably between 0.8 and 2.5 mm. According to our experiences the suspension to be sprayed is, in the majority of the cases, slightly thixotropic in nature, and liquefies even with slow stirring or even with the rhythmical suction of the pumps forwarding the suspension to the nozzle. Thus the use of viscosity-lowering additives can be avoided. The viscosity of the suspension to be sprayed is generally between 1.5° and 20E (Engler's degee). Thus it can form particles with the desired dimensions by spraying with a pressure of 5 to 20 kg./cm². The temperature of the drying medium in the spraying tower is adjusted to ensure a temperature of at least 400°C for the introduced drying medium, particularly when silicic earth-containing suspensions are sprayed, since otherwise the residence time in the spraying tower would be insufficient to ensure the complete vaporization of the liquids entrained in the pores of the grain and to ensure the optimum residual humidity content of the finished grain.

If desired, the grains obtained after spray-drying in conventional equipment are fed directly and continuously, by maintaining a very high temperature gradient, into the firing space of the highest temperature of a heat-treatment apparatus, and are strengthened by the formation of a ceramic bond. For silicic earth-based carrier substances the temperature of firing is preferably 1100° to 1300°C. With drying equipment of high capacities this operation requires at most 5 to 6 seconds, whereas this period can be considerably longer when using low-capacity drying equipment. Using spraying-firing equipments of special design, it is also possible to pass the carrier substance, as a direct continuation of the drying procedure, through a firing zone with a residence time of maximum 5 to 6 seconds, the temperature of the zone being selected so as to form the desired ceramic bond. Thus high-strength carrier substances can be prepared in a closed system with very economical energy utilization.

The porous carrier rocks suitable for carrying out the process according to the invention have been listed above. In this process clays or rocks consisting mainly of clay minerals cannot be used, since most of the pore space of these minerals is so-called intracrystal space. Although this intracrystal space can be regarded as permeable pore space with respect to the uptake of active agent, in this space the adsorption binding energy and the bond strength between the mineral and the active agent are much greater than in the simple pore spaces, termed previously as primary and secondary pore spaces. Thus the desorption of the active agent received the intracrystal space may be incomplete, and the desorption rate is correspondingly low. This relates primarily to active agents containing polar groups, such as phosphorous esters widely used in the last few years.

The applicable porous carrier rocks are selected preferably by taking into account the following criteria:

1. Rock with an original disperse structure consisting of very coarse particles, which yield smallest ground particles containing only a single pore higher in mean diameter than 500$\mu$, cannot be used in accordance with the invention, since the desired particle size of the carrier substance cannot be ensured by starting from such rocks.

2. As mentioned above, the carrier rocks are optionally subjected to pre-crushing before suspending them in water. This pre-crushing aims at rendering permeable at least 50 % of the occasionally closed pore spaces of the original rock. This pre-crushing is, however, conducted so as to obtain particles with diameters not smaller than 1$\mu$.

The pre-crushing of the carrier rock is performed by known methods. The carrier rock, either pre-crushed or not, is thereafter suspended in water preferably by subjecting it to wet grinding e.g. in a drum mill, and the pre-formed suspension of the plastic clay minerals with a known content on dry substance is added to the aqueous suspension of the carrier rock just before the termination of the wet grinding. If desired, the pre-formed suspension of said clay minerals can be allowed to stand for at least 24 hours prior to admixing it with the suspension of the carrier rock. Thereafter the suspension is further homogenized, preferably by grinding. The final limit of grinding is the particle size at which the individual particles still posses real inner pore spaces, i.e. pore spaces surrounded from all sides with rock material but are in contact with the environment through the openings between the individual rock particles. The particle size of the ground material should by no means be decreased below this critical minimum.

Alternatively, the aqueous suspension of the carrier rock can also be prepared in sludge mills. This method is suited primarily for the carrier rocks easy to suspend in water, such as silicic earth or chalk.

The plastic clay minerals also capable of binding in wet state, which can be utilized in accordance with the invention, include montmorillonite, kaolinite and its co-minerals, as well as illite. Montmorillonite is the constituent of bentonite, kaolinite is, among others, present in of kaoline, and illite is the constituent a rock also termed illite. These rocks occur in the nature either individually, or as mixed rock. Such mixed rock can also be used in the process of the invention, provided that they contain at least 60 % of the respective three clay minerals, or at least 20 % of bentonite. The most important properties of the rocks containing the three clay minerals mentioned above are summarized in Table 1.

Table 1

|  | Plasticity index (Atterberg) | Sinter temperature °C |
|---|---|---|
| Bentonite | 400 – 600 | 1000 – 1150 |
| Illite | 40 – 70 | 900 – 1000 |
| Kaolin | 20 – 50 | 1100 – 1300 |

From these data it is obvious, without any further explanation that when preparing the carrier substances according to the invention, a pre-determined amount of the three clay minerals used as plastic clay minerals capable of binding in wet state, or the respective rocks, or a combination thereof ensures the movement conditions in the sprayed droplets and the bond strengths in dry state that result in the above-described characteristic internal structure of the carrier grain and make possible a thermal strengthening of the grains by an optional firing step. No generally valid rules can be given for the mixing ratios of the three clay mineral types, since the most appropriate mixing ratio also depends on the particle size and distribution of the suspended rock particles even when the same carrier rocks are concerned. Thus the most appropriate plastic clay mineral combinations ensuring optimum consistency in the suspension should be determined by preliminary experiments. These experiments can be carried out by methods well known in the art.

It is generally not necessary to use other additives beside the three clay minerals in the process of the invention, since the appropriate combination of said clay minerals in itself ensures all the essential conditions for the preparation of the carrier. It may be advantageous, however, to add some other additives to the mixture in order to modify the surface polarities or wetting properties of the carrier rocks, primarily when no firing is performed after spray-drying, i.e. when the carrier substance is used without any after-treatment.

The carriers according to the invention are suitable for formulating any biologically active substance, such as herbicidal or pesticidal, e.g. insecticidal, fungicidal, acaricidal or nematocidal agents. In other words, these carrier substances are capable of absorbing any liquid or liquefied (e.g. molten) active agent, and the thus-obtained formulation is storable and provides efficient and complete desorption of the active agent when the composition is used. Furthermore, the sorptional carriers according to the invention can also be formulated with gaseous substances or substances liquefied under pressure. In this latter instance the grains should be provided, after the uptake of the active agent and decomposable when the composition is used, with a coating impermeable to the active agent.

The non-fired and fired sorptional carriers according to the invention can be used essentially for the same purposes, but when non-fired carriers are used, the lower strength of the carrier should be taken into account. It should also be considered that non-fired carriers cannot be used in combination with active agents in aqueous media.

The carriers according to the invention, particularly the fired ones, are resistant to deterioration by acids and alkalies, with the exception of hydrogen fluoride.

The carriers according to the invention are perticularly suitable for the formulation of substances with systemic actions, since in this instance the desorption of the active agent can be controlled.

The simplest method of applying the active agent onto the carrier according to the invention is the slow and continuous addition of the active agent to the stirred carrier. One may also proceed, however, by adding the active agent batchwise, and homogenizing the mixture of the carrier and active agent prior to the addition of the next batch. Toxic or volatile active agents can be admixed with the carrier in a closed drum by injecting or spraying the active agent into the drum. It is preferable to allow the formulation to stand for a while in closed drums prior to packing.

The invention is elucidated in further detail in the following non-limiting Examples.

EXAMPLE 1

180 kg. of a Hungarian silicic earth (diatomaceous earth) with a humidity (moisture) content of 43 %, containing in homogeneous distribution about 5 % of montmorillonite, about 3 % of illite and about 4 % of slightly limonitic kaolin are suspended in 100 l. of water using a wing propeller, and the obtained suspension containing 36 % of dry material is permitted to stand for one day. A suspension of 84 cP viscosity and 1250 g./l. specific gravity is obtained. This suspension is homogenized in a sludge mill for 30 minutes, then sprayed through a nozzle with an opening of 0.9 mm., at a pressure of 17 to 18 kg./cm$^2$., using a drying air which enters the spray-drier at a temperature of 400°C (the temperature of the exiting air is about 95° to 110°C). A substance with a residual humidity content of 10 to 12 % is obtained. Spherically shaped grains, with a strength sufficient to be transported in bags, are obtained. The particle size distribution of the obtained substance is as follows:

| | |
|---|---|
| 0.4 to 1.0 mm. | 7.0 % |
| 0.25 to 0.4 mm. | 65.0 % |
| 0.10 to 0.25 mm. | 26.0 % |
| below 0.10 mm. | 2.0 % |

The obtained substance is strengthened in a roll-over furnace at 1140° to 1200°C with a residence time of 40 minutes. The sorption capacity of the obtained carrier substance, determined with n-xylene, is 84 %.

EXAMPLE 2

Pumice stone originating from the mountain Mátra (Hungary) and having a slightly slacking, fine fibrous-laminar structure, is used as carrier rock. The crude rock is precrushed with a jaw breaker to a particle size below 10 mm., suspended in water in a concentration of 40 %, and ground in a ball mill until a sample occasionally removed from the mill does not leave residue when sludged on a sieve with 40µ openings. The obtained suspension is subjected to simple sedimentation and suction in order to remove the fraction smaller than 5µ, since the grains of this latter fraction contain no pore space. The purified suspension is diluted to a volume of 50 liters, to obtain a suspension with a dry material content of 38 %. 68 % of the particles contained in this suspension are smaller than 20 µ. Thereafter 3 kg. of air-dry bentonite is added, which contains, on the basis of X-ray analysis, 27 % of montmorillonite and about 7 % of illite, and contains as residue quartz in the major part and kaolinite in the minor part. Furthermore, 1 kg. of an illite rock consisting practically entirely of illite is added to the suspension. The suspension is homogenized for 3 hours in a sludge mill, to obtain a suspension with a dry substance content of 35 % and a specific gravity of 1265 g./l. This suspension is spray-dried in a pilot-plant apparatus, having a nozzle with an opening of 0.9 mm., under a pressure of 15 kg./cm$^2$. and with drying air entering at a temperature of 400°C. A carrier substance consisting of grains greater than 0.2 mm. in diameter is obtained. This carrier substance is fired at 1000°C for 25 minutes in a laboratory-scale mantle furnace. The sorption capacity of the fired substance is 58 %, and its relative grain strength is very favorable.

EXAMPLE 3 (Comparative example)

The data of this Example show the disadvantages resulting from the use of suspension containing less than 30 % of dry material.

2650 kg. of a diatomaceous earth with the same composition and humidity content as described in Example 1 are ground with 2350 l. of water in a sludge mill to obtain a suspension containing 28.5 % of dry material. After 3 hours of milling, a suspension with a viscosity of 1.4°E is obtained.

The resulting suspension is spray-dried under the following conditions: nozzle diameter: 1.8 mm., pressure: 17.5 kg./cm$^2$., temperature of entering air: 650°–700°C. A granular substance with a residual humidity of 2 to 3 % is obtained. In this carrier substance the amount of the fraction with a particle size less than 0.1 mm. is between 2.5 and 6.1 %, depending on the time of sampling, and the amount of the fraction with a particle size between 0.1 and 0.25 mm. is 45 to 55 %. These data, compared with the granulometric distribution given in Example 1, clearly show the basic effect of the suspension concentration on the grain structure. The other characteristics of the obtained carrier substance proved to be appropriate.

In order to check whether the high temperature of the drying medium affects the formation of droplets, the above experiment was repeated at a temperatue of 600°C. In this instance agglomerated grains appear in the product, which indicates inappropriate drying, but no change can be observed in the particle size distribution.

EXAMPLE 4

1.4 tons of a granular substance with a residual humidity content of 2.4 %, prepared as described in the first paragraph of Example 1 but in a large-scale equipment, are introduced into an industrial roll-over furnace equipped with oil burners. The technical parameters of the furnace are as follows: slope: 17°, internal diameter: 70 cm., length: 5 m., capacity of the burners: 300 kg. of light fuel oil per hour. The furnace is attached to a storage space open towards the environment, from which the fired substance is removed by a ventilator system and forwarded into containers via three separation cyclones. The cyclones are equipped with water cooling to cool simultaneously the product.

The granular substance is fed directly into the fire space of the furnace at a rate of 1.4 tons/hour. The temperature of the fire space is about 1250°–1350°C. At this temperature the fed substance is solidified sufficiently during the residence time of 4 to 5 seconds, without sintering or losing the favorable dimensional and structural properties of the individual grains. The rate of temperature rise in the granular substance is about 300°–350°C/sec. Care should be taken to the uniformity of feeding and heating, since these parameters have essential effects on the mechanical stability of the final grains. Excessive surface melting must be avoided, since it would impair the sorption capacity of the granular substance, and the grains would deposit onto the furnace walls thereby causing awkward operational difficulties.

According to our experiences the firing of the granular substance can be performed with excellent results in conventional perlite-expanding furnaces.

What we claim is:

1. A porous carrier rock-based sorptional carrier consisting of at least one porous carrier rock selected from the group which consists of silicic earth, pumices, tuffs, bubble-porous lava rocks, expanded perlite, vermiculite, chalks, other porous biogeneous limes, and porous sand rocks in an amount not exceeding 95% by weight and 5 to 30% by weight of a clay mineral in a particle size of about 0.1 to 1$\mu$ and selected from the group which consists of montmorillonite, illite, kaolinite, and co-minerals thereof provided that montmorillonite is present in an amount of at least 5% by weight, having a multiple sorptional pore space, possessing a sorption capacity of at least 50%, and being quasi-spherical in shape.

2. A carrier as defined in claim 1, containing silicic earth as carrier rock.

3. A carrier as defined in claim 1, containing at least 5 % by weight of montmorillonite and 10 to 25 % by weight of illite.

4. A process for the preparation of a sorptional carrier for biologically active material comprising the steps of:

wet-grinding at least one porous carrier rock selected from the group which consists of silicic earth, pumices, tuffs, bubble-porous lava rocks, expanded perlite vermiculite, chalks, other porous biogeneous limes, and porous sand rocks, and suspending same in water with a quantity of a plastic clay mineral of about 5 to 30% by weight of the carrier rock, said porous clay mineral being selected from the group which consists of montmorillonite, illite and kaolinite and cominerals thereof such that montmorillonite is present in an amount of at least 5% by weight of the carrier rock;

adjusting said suspension so that the dry solids thereof are present in said suspension in an amount of at least 30% by weight;

intensely stirring said suspension to homogenize the same; and spray-drying the homogenized suspension though a nozzle having an orifice of at least 0.8 mm diameter in a gas stream having a temperature of at least 400°C to produce particles of 0.1 to 1.5 mm in diameter.

5. The process defined in claim 4 wherein the particles of 0.1 to 1.5 mm in diameter are fired at a temperature of 900° to 1300°C.

6. The process defined in claim 5 wherein said clay mineral is present in an amount of 8 to 20% by weight of the carrier rock and the firing is carried out for a period of 3 to 6 seconds.

* * * * *